United States Patent [19]

Ritchart et al.

[11] Patent Number: 4,994,069
[45] Date of Patent: Feb. 19, 1991

[54] VASO-OCCLUSION COIL AND METHOD

[75] Inventors: Mark Ritchart; Mike Mariant; Ivan Sepetka, all of Santa Clara; Erik Engelson, Portola Valley, all of Calif.

[73] Assignee: Target Therapeutics, San Jose, Calif.

[21] Appl. No.: 265,908

[22] Filed: Nov. 2, 1988

[51] Int. Cl.$^5$ .................. A61B 17/12; A61B 17/00
[52] U.S. Cl. .................. 606/191; 606/198; 606/200; 604/104; 623/1; 623/11
[58] Field of Search ........... 606/194, 198, 200, 191; 604/104; 623/1, 11, 12

[56] References Cited

U.S. PATENT DOCUMENTS

| 3,334,629 | 8/1967 | Cohn | 606/194 |
| 3,868,956 | 3/1975 | Alfidi et al. | 606/198 |
| 4,494,531 | 1/1985 | Gianturco | 606/200 |
| 4,655,771 | 4/1987 | Wallsten | 623/1 |
| 4,865,516 | 8/1989 | Hillsted | 604/104 |

FOREIGN PATENT DOCUMENTS 0183372  6/1986  European Pat. Off. ............. 623/12

Primary Examiner—Randall L. Green
Assistant Examiner—Paul Prebilic
Attorney, Agent, or Firm—Irell & Manella

[57] ABSTRACT

A flexible, preferably coiled wire for use in small-vessel vaso-occlusion. The wire has a stretched, linear condition in which it can be advanced through a catheter lumen to a selected vessel, and a relaxed, convoluted condition produced by a combination of a helical winding of the wire, and irregularities of the helical winding. When the wire is released from a catheter into a vessel, it assumes a randomly coiled, substantially space-filling mass which is lodged at the site of release. In a preferred embodiment, the helical winding in the wire's relaxed condition has about the same diameter as that of the vessel, and the wire, in its stretched condition, has a length of about 15–20 times the vessel diameter.

25 Claims, 2 Drawing Sheets

VASO-OCCLUSION COIL AND METHOD

FIELD OF THE INVENTION

The present invention relates to vaso-occlusion devices and methods, and in particular to coiled wires designed for delivery through a catheter at an occlusion site.

References

Ethanasoulis, C. A., *New Eng J Med* (1980), 302:(20)(21).
Berenstein, A., et al, *Radiology* (1979), B2:631.
Battista, O. A., et al, *J. Appl. Polyser Sci* (1967), 11:481.
Hilal, S. K., et al, *J. Neurosurg* (1975), 43:255.
Kaufman, S. L., et al, *Investigative Radiology* (1978), vol. 1, no. 3, pp. 200–204.
Kumar, A. J., et al, *J Neuroradiology* (1982), 3:163–168.
Latchow, R. E., et al, *Radiology* (1979), 131:669.
Reuter, S. R., et al, *AJR* (1975), 125:119–126.
Roberson, G. H., et al, *AJR* (1979), 133:657.
Wallace, S., et al, *Cancer* (1979), 43:322–328.

BACKGROUND OF THE INVENTION

Endovascular therapy has been used in treating a variety of conditions, such as in controlling internal bleeding, occluding blood supply to tumors, and relieving vessel-wall pressure in a region of a vessel aneurism (Athanosoulis, Wallace, Reuter).

The embolic agent may be an injectable fluid, such as a microfibrillar collagen (Battista, Kaufman, Kumar), Gelfoam (Berenstein, Roberson) silastic beads (Hilal), and polyvinyl alcohol foam (Latchaw). Co-owned U.S. patent application Ser. No. 823,635 describes a cross-linked vaso-occlusive agent whose persistence at a vaso-occlusive site can be extended up to several months, depending on the degree of cross-linking. These fluid agents can be injected into a selected vessel site through a catheter, and there gel into a solid, space-filling mass at the injection site. Typically such fluid agents provide good short-term vaso-occlusion, but are ultimately resorbed in the process of vessel recanalization.

Polymer resins, such as cyanoacrylate resins, have also been employed as an injectable vaso-occlusive material. Like injectable gel materials, the resins are typically mixed with a radiocontrast material in order to be seen fluoroscopically. A risk with this material is inadvertent embolism in normal vasculature due to the inability to control the destination of pre-gelled resins. The material is also difficult or impossible to retrieve, once placed.

Two types of mechanical vaso-occlusion devices are known. The first is a balloon which can be carried to the vessel site at the end of a catheter, and there inflated with a suitable fluid, typically a polymerizable resin, and released from the end of the catheter. The balloon device has the advantage that it effectively fills the cross section of the occluded vessel. A vascular balloon is difficult or impossible to retrieve after the resin in the balloon sets up, and the balloon cannot be visualized unless it is filled with a contrast material. Also the balloon can rupture during filling, or release prematurely during filling, leaking monomer resin into the vasculature.

A second type of mechanical vaso-occlusive device is a wire coil which can be introduced through a catheter in a stretched linear form, and which assumes a helical wire shape when released into a vessel. In vaso-occlusion coils used heretofore, the wire itself is a relatively stiff, shape-retaining stainless steel coil. The wire is shaped to have 1–2 helical windings dimensioned to engage the walls of the vessel. The wire is also coated with filaments, such as dacron or cotton fibers, which provide a substrate for clot formation in the interior region of the vessel, while the coil itself serves to anchor the device on the vessel wall at the site of release. This type of coil is also known as a Gianturco coil (Cook Corp, Bloomington, Ill.). The coil is relatively permanent, can be imaged radiographically, can be located at a well-defined vessel site, and has the possibility at least of being retrieved. A limitation of fiber-coated coils is that recanalization of the vessel can occur, presumably by resorption of the clot by endothelial cells. Further, the fiber-coated coils are difficult to introduce into vessel sites which require tortuous path access and/or involve vessel size less than about 1–3 mm. This is because a fiber-coated coil is generally too stiff and has too high a frictional coefficient to be readily advanced through a small-diameter catheter, especially in a region of catheter bends.

SUMMARY OF THE INVENTION

It is therefore a general object of the present invention to provide a vaso-occlusion wire which has the advantages of existing vaso-occlusion coil wire devices, but overcomes the above-mentioned limitations of such devices.

It is a more specific object of the invention to provide such a wire capable of forming a convoluted, substantially space-filling mass when introduced into a vessel.

It is another specific object of the invention to provide such a wire which can be easily advanced through a flexible, small-diameter catheter.

It is still another object of the invention to provide a vaso-occlusive coil which can be retrieved from a vessel site by a catheter wire tool.

Providing a catheter system and method of vaso-occlusion is still another object of the invention.

The present invention includes a flexible, vaso-occlusive wire designed for occluding a vessel having a selected crosssectional area, when the wire is released into the vessel from a small-diameter catheter. The wire is characterized by:

(a) a relaxed condition in which the wire assumes a folded, convoluted conformation which is adapted to form a substantially space-filling mass when the wire is released into the vessel, (b) a stretched condition in which the wire has a linear configuration in which the wire can be pushed through the catheter, and (c) a memory which returns the wire from its stretched to its relaxed condition, as the wire is released from the catheter into the vessel, thus forming a space-filling, vaso-occlusive mass which is lodged in the vessel at the site of release.

In a preferred embodiment, the relaxed conformation of the wire is produced by a combination of a helical winding in the wire which has a winding diameter substantially that of the vessel to be occluded, and irregularities in helical winding which cause the wire to adopt a substantially random folding pattern when released from a catheter into such a vessel. The irregularities in the helical conformation may be produced by bends in the windings and/or variations in the coil wrapping which predispose the wire to bend in certain directions.

Also in a preferred embodiment, the wire in its stretched condition is a coiled wire formed by helical wrappings of a metal thread, preferably platinum, tungsten, or gold thread. The diameter of coiled wire is preferably between about 10-30 mils. The length of the coiled wire is at least about 15-20 times the diameter of the vessel to be occluded.

In another embodiment, the winding which characterizes relaxed conformation has a spiral shape dimensioned to fill the cross section of the vessel to be occluded.

The wire may be coated or filled with a water-soluble material which acts to hold the wire in its linear condition until the material is contacted with aqueous medium, either in the delivery catheter or at the vessel site. Alternatively, the wire may be coated or filled with a drug-release material designed to provide slow release of a drug from the wire at the vessel site.

Also forming a part of the invention is a catheter system for use in occluding a vessel having a selected cross-sectional area. The system includes a vaso-occlusion wire of the type described above, and a small-diameter catheter which is designed for delivering the coil to a selected site in a small vessel, e.g., 0.5 to 6 mm diameter vessel. The catheter is preferably designed for accessing a vessel site along a tortuous vessel path. Also included in the system is a pusher for advancing the occlusion wire through the catheter. The pusher has a relatively stiff proximal segment which extends over most of the pusher length, and a relatively flexible distal portion formed of an extruded polymer, preferably a fluorocarbon polymer.

The system may further include a retrieving wire effective to penetrate the space-filling mass of vaso-occlusion wire in the vessel. The retrieving wire preferably adopts a preformed corkscrew shape as it is released from the catheter, for engaging the convoluted windings of the vaso-occlusion wire.

In another aspect, the invention includes a method employing the above system for producing vaso-occlusion at a small-vessel site. The method may be used to achieve permanent vaso-occlusion in a small vessel, vaso-occlusion with depot drug release from the vessel site, and/or vaso-occlusion with a temporary backfill of a fluid material, such as collagen or a drug or contrast-containing material. In the latter method, the vessel region immediately upstream of the vaso-occlusion wire is filled with the fluid through the catheter after wire placement. The method may further include a procedure for retrieving the wire from the vessel.

These and other objects and features of the invention will become more fully apparent when the following detailed description of the invention is read in conjunction with the accompanying drawings.

DETAILED DESCRIPTION OF THE INVENTION

Figure 1:
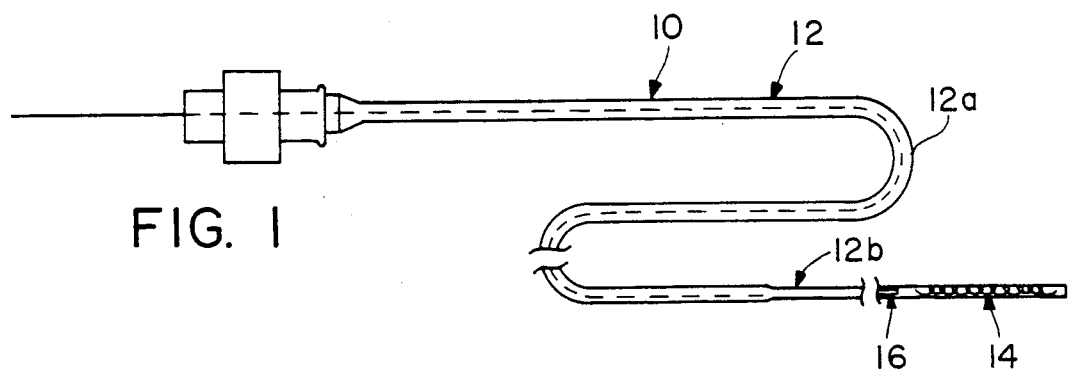
FIG. 1 is a fragmentary view of a catheter system used for delivering a vaso-occlusion wire according to the invention.

FIG. 1 shows a catheter system 10 composed of a small-diameter catheter 12, a vaso-occlusion wire 14 constructed according to the invention, and a wire pusher 16 for advancing wire 14 through the catheter. The construction and characteristics of wire 14, and alternative-embodiment vaso-occlusive wires, are detailed in Section A. Section B describes the catheter system, including pusher 16 and a retrieving wire used for removing the wire from a vessel. The operation of the system for use in placing the wire at a selected site in a vessel is given in Section C.

A. Vaso-Occlusion Wire

Figure 2A:
FIGS. 2A-2C show the stretched, linear conformation of a vaso-occlusion wire formed by a helically coiled wrapping (2A), the helical winding formed in the wire (2B), and the irregularities in the helical winding (2C) in the relaxed condition of a wire constructed according to one embodiment of the invention.
Figure 2B:
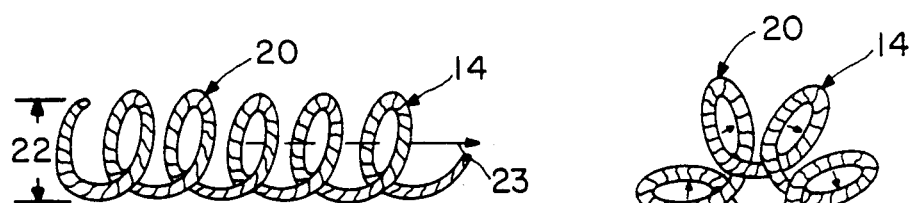
Figure 2C:
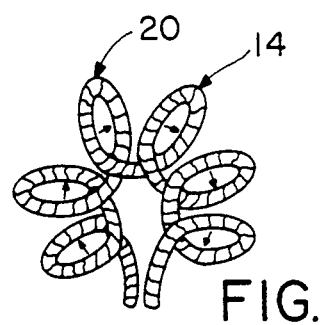

The steps in the construction of vaso-occlusion wire 14 are illustrated in FIGS. 2A-2C. The wire itself is formed by wrappings or windings of a fine wire thread 18, preferably 0.002 mils to 0.006 mils platinum, tungsten, or gold thread which is available, for example, from California Fine Wire Company (Grover City, Calif.). The windings are preferably made by wrapping the thread on a spinning mandrel, according to known coil-manufacturing methods. The wire advance on the mandrel is adjusted to produce a single-layer coil with a minimum helical pitch, i.e., in which the windings are close packed. Typically, the mandrel has a diameter of between about 5-25 mils (1/1000 inch), yielding a coil wire whose outer diameter is between about 10-30 mils. The soft, flexible coil produced on the mandrel is cut to desired lengths after removal from the mandrel. For wires intended for use in vessels with diameters of about 2 mm and smaller, the wire has a preferred length of about 3-6 cm. For vessels in the 2-6 mm size range, wire lengths of between about 5-10 cm are preferred.

The coiled wire is wound on a larger-diameter mandrel to form a helical winding 20 whose helix diameter, indicated at 22, is approximately that of the vessel for which the coil is intended. The helical axis is indicated at 23. Thus, for a wire designed for vaso-occlusion of a vessel of about 2-6 mm, the diameter of the helical winding formed is preferably 2-6 mm, respectively. It is noted, however, that a wire winding of about 2 mm diameter is also suitable for the smallest vessels which can be occluded by the present invention, in the range of about 0.5 to 2 mm. It can be appreciated from the above-mentioned wire lengths and winding diameters, that the wires typically will contain 4-8 helical windings, as illustrated in FIG. 2B.

The wire is further preformed to contain irregularities in the helical winding, such that the wire adopts a folded, convoluted conformation in a relaxed condition, as illustrated in FIG. 2C. As seen, the irregularities in this embodiment are such as to offset the helical axis (indicated by arrows in the figure) of each winding by 20-40 degrees. The irregularities are preferably made by deforming, as by twisting, the wire in the region of desired bends with the wire on the helical winding mandrel. The wire is treated by heating at about 800° F. for 24 hours for memory retention after it is shaped.

According to an important feature of the invention, the combination of the helical winding and the irregularities in the winding cause the wire to form a randomly shaped, substantially space-filling mass when released into a vessel, as will be illustrated below. In particular, the memory in the wire is effective to return the wire from a stretched, linear condition in which it is advanced through a catheter to a randomly oriented, space-filling relaxed condition as the wire is released from the catheter. The high memory in the wire is achieved, in part, by the overall length of the thread used in forming the wire, i.e., the high ratio of thread length:change in wire shape.

The wire just described may be thought of as having a primary structure formed by the coil wrapping making up the wire, a secondary structure formed by the helical winding, and a tertiary structure formed by the irregularities in the winding. It will be appreciated that the random shape of the wire in its relaxed condition can be achieved by other, related secondary structures in the wire, such as a series of arcs which are interrupted at intervals by bends which orient the arcs in different directions.

Figure 3A:
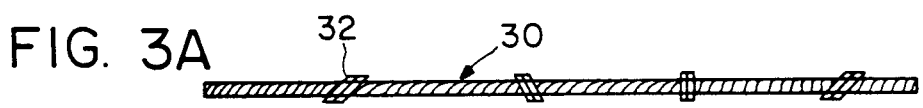
FIGS. 3A and 3B illustrate an alternative embodiment of the wire invention, in which the helical wrapping forming the wire has regions which are flattened or elliptical in random direction, when the wire is in a stretched condition (3A), causing the winding in the wire to assume a random, convoluted shape (3B) when in a relaxed condition.
Figure 3B:
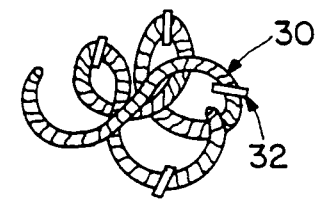

FIGS. 3A and 3B illustrate a vaso-occlusion wire 30 which is formed as described above, but where the irregularities in the helical winding are produced by flattening the wire coil in different directions. This is done, for example, by squeezing the coil wire at several regions along the winding, such as region 32, each at different angles with respect to the wire axis. The wire so formed will have the general appearance shown in FIG. 3A when stretched to its linear condition, and the appearance shown in FIG. 3B in its relaxed condition. The flattened regions of the coil must, of course, be less than the inner diameter of the catheter used in delivering the wire in its stretched condition. The flattened coil embodiment just described has the advantage that the flattened regions enhance the wire memory, i.e., predispose the wire toward its preformed, relaxed condition when it is released into a vessel.

Figures 4A, 4B:
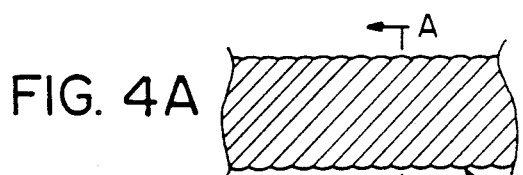
FIG. 4A and 4B illustrate an embodiment of a coil wire which is filled with a water-soluble stiffening material, shown in a stretched condition (4A) and in a cross section (4B) taken through line A—A in FIG. 4A.

FIG. 4A shows a vaso-occlusion wire 34 formed according to another embodiment of the invention. The wire differs from wire 14 in that its inner wall region is coated with a rigid, water-soluble material 36, as seen in the cross sectional view in FIG. 4B. This material may be any biocompatible crystalline, non-crystalline, or a water-soluble material, such as agarose, collagen, a sugar, or the like, which can be applied to the interior wire region and dehydrated, as by reduced pressure, to form a rigid shell within the wire coil. It will be recognized that the rigidfying material may alternatively coat the outer wall or encapsulate the wire coil.

Figure 5:
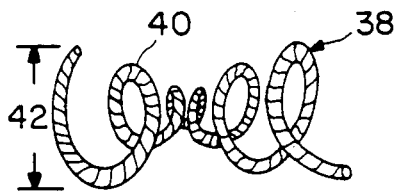
FIG. 5 illustrates a vaso-occlusion wire constructed according to another embodiment of the invention, and shown here in a relaxed condition.

A vaso-occlusion wire 38 formed according to another embodiment of the invention is shown in FIG. 5. The wire has a coiled primary structure, formed as above, and a helical winding 40 having at least about 1 helical turn whose diameter, indicated at 42, is approximately that of the vessel to be occluded. In this embodiment, the irregularities in the helical winding take the form of continuous change in helical diameter, forming spirals which are dimensioned to span the cross-sectional area of a vessel.

Figure 6:
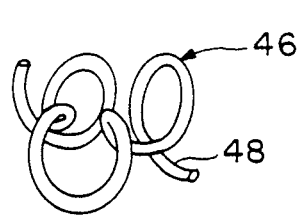
FIG. 6 illustrates another embodiment of the invention, in which the wire is formed of a polymeric tube containing a drug for slow release.

FIG. 6 shows a vaso-occlusion wire 46 formed from a flexible, preshaped polymer tube 48. That is, the wire does not have a primary structure (wire coil) but has a secondary and tertiary structure formed by a combination of a helical winding and irregularities in the winding. The wire can be formed from a straight section of rod or tube, where the helical winding and winding irregularities are imparted during heat treatment, or by shaping the wire as it is extruded, before cooling, or by injection molding. Suitable polymers for use in preparing this type of wire include any biocompatible, polymer such as polyethylene, polyurethane, polypropylene, and the like, which is capable (by its inherent memory) of substantially reversible shape-retention between stretched and preformed, relaxed conditions.

After wire formation, the interior of the tube may be filled with a drug material, such as a sterile drug concentrate, and its ends partially sealed for slow drug release from the tube, in an aqueous environment. The ends of the tube can be sealed by a water-soluble plug for storage.

B. Vaso-occlusion Catheter System

With reference again to FIG. 1, catheter 12 used in delivering the vaso-occlusion wire is a flexible, small-diameter catheter designed for use with a guidewire (not shown) for accessing small-vessel sites within a body. The vessel to be accessed has a diameter typically between about 0.5-6 mm, and may include any arterial or venous vessel, or an organ duct, such as a bile duct, which can be accessed by a small-diameter catheter. In particular, the site to be accessed may be along a soft-tissue, tortuous-path vessel, such as a deep-brain site. One preferred catheter construction is described in co-owned U.S. Pat. No. 4,739,768 for "Catheter and Tissue-Accessing Method". Briefly, this catheter has a relatively stiff proximal section 12a suitable for advancing the catheter tube along a guide wire from an access site to the tissue of interest, and a relatively flexible proximal section 12b about 10-50 cm in length, designed to track the guide wire along a tortuous path in the tissue.

Figure 7:
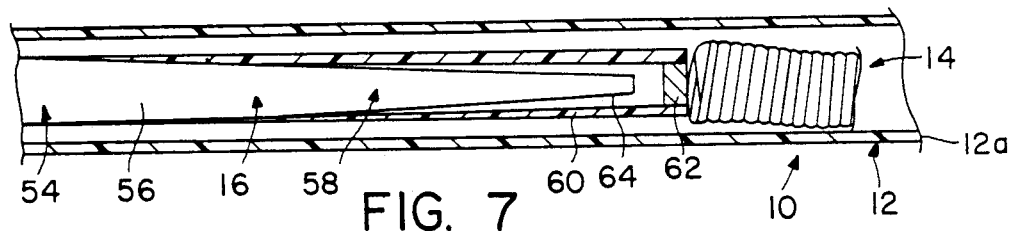
FIG. 7 shows enlarged, fragmentary portions of a catheter system of the invention.

FIG. 7 shows an enlarged fragmentary portion of the catheter system, including pusher 16 and vaso-occlusion wire 14. The inner diameter of the catheter is typically about 40-80% larger than the diameter of the wire, e.g., between about 14-18 mils for a 10-mil diameter wire, and between about 42-54 mils for a 30 mil diameter wire.

Pusher 16 has a novel construction which is specially designed for advancing wire 14 through the catheter positioned along a tortuous path. The problem faced in advancing the stretched wire through a catheter is that considerable axial force must be applied to the wire, to overcome the frictional force produced by the preformed wire against the sides of the catheter. The limitation of using a guide wire for this purpose is that when the catheter is positioned in a tortuous vessel path, a guide wire flexible enough in its distal section to follow along this path may not provide the column strength necessary to advance the wire axially. For example, the distal end of the guidewire may be a tapered wire covered by a soft flexible coil tip, and this structure can readily buckle as it is forced against the wire where sharp bends in the catheter are encountered. Reducing the guidewire flexibility increases the probability that the that the wire will either be too difficult to advance through the catheter, or that the catheter will be repositioned as the guide wire is advanced. Also, a guide wire may have a tapered distal portion which can overlap the coil wire inside the catheter. Ideally then, the pusher should be fabricated from a material that has high column strength, good flexibility, and a low frictional coefficient.

Pusher 16 which achieves these goals is formed of a relatively stiff proximal portion 54 preferably fabricated from a constant-diameter portion of a stainless steel wire 56 or the like, and a distal portion 58 composed of low-friction polymer tubing 60, preferably a fluorocarbon polymer (Teflon TM) tubing, formed by known extrusion methods and an inner tapered portion of the wire. The proximal portion provides high column strength and torqueability in a more proximal region of the catheter where flexibility can be sacrificed. The distal region provides relatively high column strength, good flexibility, and low frictional coefficient.

The outer diameter of the polymer tube is preferably about 75% of the catheter inner diameter, to prevent the pusher from overlapping the wire inside the catheter. The length of the tubing in the pusher is typically between about 25-50 cm. The distal end of the tubing is filled with a radio-opaque plug 62 formed of gold, platinum, or tungsten, or is provided with a radio-opaque band.

Wire 56, whose constant-diameter region forms the proximal portion of the pusher, is preferably a straightened stainless steel wire having an outer diameter of between about 8-25 mils, and preferably slightly less than that of the associated extruded tubing, but in any case, within about 30% of the tubing diameter. The wire is joined to the tubing by forming a tapered distal end region 64 in the wire, for example, by grinding. The length of the tapered region is typically between about 25-50 cm. In the usual case, the inner diameter of the tube is less than that of the untapered portion of the wire so that when the tube is placed on the wire initially, it covers only a portion of the tapered region of the wire. The tube can be forced over the remaining tapered wire region by heating the proximal tube region, e.g., the proximal 10-25 cm, to a temperature of between about 400°-600° F. and forcing the heated tube over the wire until the tube's proximal end is approximately flush with the wire's taper boundary. The heated tube is now pulled distally, stretching and "thinning" the tube in its heated region, with the heated, thinned portions of the tube adhering to the proximal portion of the tapered wire region. As seen from FIG. 7, the stretching operation produces a smooth tapered interface where the tube is joined to the wire typically covering about 10-25. According to an important feature of the invention, the proximal-to-distal taper in the wire, and the distal-to-proximal taper in the tubing act to produce a substantially smooth, i.e., monotonic transition in pusher flexibility in progressing from the more rigid wire to the more flexible tubing. One preferred pusher, for use with a 21 mil inner diameter inner diameter catheter, is formed by joining a 40 cm Teflon TM tube, 14-17 mils outer diameter, 4-5 mils inner diameter to a 100-200 cm stainless steel wire, 14-18 mils diameter and having a 40 cm taper down to a final diameter of about 2-4 mils.

Figure 9A:
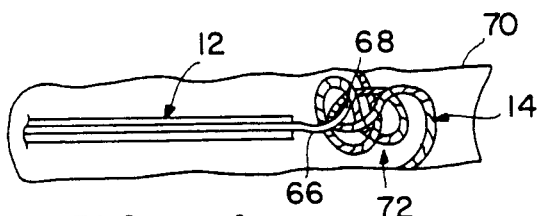
FIGS. 9A-9C illustrate steps in the retrieval of a space-filling wire within a vessel.
Figure 9B:
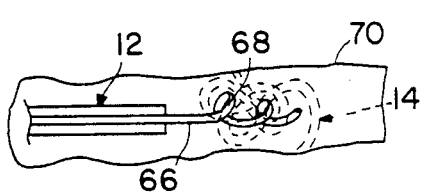
Figure 9C:
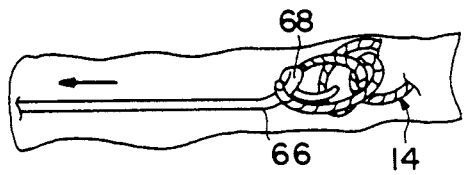

The vaso-occlusion system of the invention may also include a retrieving wire 66 shown in FIGS. 9A-9C. This wire has the same general dimensions as the guidewire used for catheter placement, but differs from a standard guidewire in that the distal end is preformed to adopt a corkscrew-like looped end 68 after it is advanced beyond the end of the catheter. The operation of the system, including that of the retrieving wire will now be described.

C. Vaso-occlusion Method

The method of occluding a selected site in a vessel is illustrated in FIGS. 8A-8D. The figures show a portion of a vessel 70 which is to be occluded at a selected site 72, and the distal end region of catheter system used in practicing the method. As indicated above, the vessel may be located along a tortuous vessel path characterized by relatively small vessels, e.g., less than 2-4 mm in diameter, and sharp vessel bends, within a soft tissue, such as a deep brain vessel site.

Initially, catheter 12 in the system is guided to the selected site by standard guidewire/catheter procedures in which a guidewire with a bent end tip is guided by torquing along the selected vessel path, either by moving the guidewire and catheter as a unit, or by alternately advancing the guidewire, then the catheter. After reaching the selected vessel site, the guidewire is removed.

The vaso-occlusion wire is preferably supplied in prepackaged form in a sterile canula (not shown) which is adapted to engage the proximal end of the catheter. With the catheter placed at the desired vessel site, the canula is attached to the catheter and the wire is transferred into the catheter by a short guidewire. The canula is then removed and the pusher is used to advance the wire through the catheter. Alternatively, the wire may be supplied in a straight rigidified form, such as described for wire 34 above. In this form, the wire can be easily threaded into a catheter, where contact with fluid in the catheter dissolves the material which is maintaining the coil in a linear conformation.

Figure 8A:
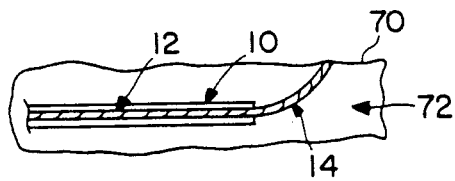
FIGS. 8A-8D illustrate the formation of a convoluted, substantially space-filling mass as the vaso-occlusion wire of the invention is released from a catheter into a vessel site.
Figure 8B:
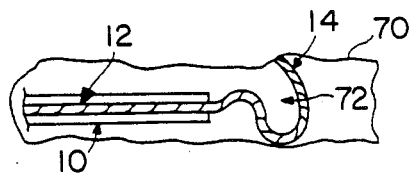
Figure 8C:
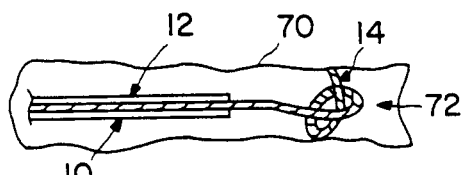
Figure 8D:
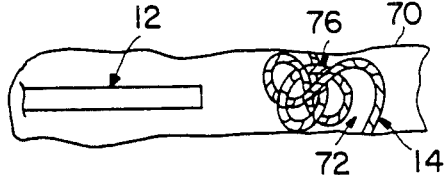

As seen in FIG. 8B, the wire initially contacts the vessel wall as it is pushed out of the catheter, with continued wire advance forcing the wire to engage the vessel along a section of the helical winding and/or against the opposite side wall of the vessel. At this stage, the wire is anchored in the vessel by the arcuate contact between the wire and vessel wall, as can be appreciated from FIG. 8B. With continued release of the wire from the catheter, the irregularities in the wire winding cause wire folding toward a space-filling, ball-like mass, as indicated in FIG. 8C. The vaso-occlusion mass formed after complete release of the wire is shown at 76 in FIG. 8D. The catheter is then be withdrawn to complete the vaso-occlusion method.

The sequence of events shown in FIG. 8A-8D illustrate two features of the wire folding events which take place in the vessel. First, the wire will engage and become anchored to the sides of the vessel wall at the site of wire release, regardless of the initial disposition between the wire and vessel wall. This is because the helical winding in the wire will initially contact a side wall of the vessel, then be forced into contact against an opposite wall portion of the vessel. Secondly, as has been confirmed by many in vivo vaso-occlusion studies conducted in support of the present invention, the wire in all cases adopts a randomly coiled, space-filling conformation when released into the vessel. This is due to the fact that (a) the wire region being released is constrained axially between the catheter end and the adjacent site of wire anchorage, and (b) the axial constraint is accommodated by irregularities in the helical winding which bias the wire in seemingly random directions as it is released from the catheter. Note that the random, space-filling conformation within a vessel does not necessarily correspond to the initial preformed relaxed condition of the wire, nor is it necessarily the condition which would be adopted if the same wire were released into the vessel a second time.

Figure 10:
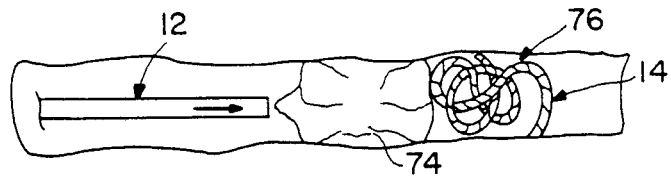
FIG. 10 illustrates a vaso-occlusion method in which the vaso-occlusion wire in a vessel is backfilled with a drug-contained collagen bolus.

In another embodiment of the method, illustrated in FIG. 10, pusher 16 is withdrawn from the catheter, and a vaso-occlusive fluid material, such as a collagen bolus 74, is injected as backfill against the wire mass. The space-filling vaso-occlusion wire here provides a substrate or matrix against which the injected fluid material can be trapped. The injected fluid material may contain entrapped drug or hormone compounds, for depot release from the bolus site as the trapped fluid material is slowly replaced in the vessel. Thus for example, in tumor treatment, the vaso-occlusion coil can reduce blood supply to the tumor, and/or be used to potentiate hyperthermic treatment. At the same time, an injected bolus material can provide slow, target-directed drug release into the tumor.

In still another embodiment of the method, drug release from a selected vascular site is achieved by inserting a vaso-occlusion wire, such as wire 46, designed for depot drug release from the wire in situ.

In another aspect, the method of the invention allows for retrieval of the vaso-occlusion wire from a vessel site, e.g., following tumor therapy. This is done with use of the retrieval wire described above, and as illustrated in FIGS. 9A-9C. With reference to these figures, a catheter 12 is positioned immediately adjacent the vaso-occlusion site, and the guide wire is replaced with retrieval wire 66. As seen in FIGS. 9A and 9B, as the wire end is advanced into the random vaso-occlusion mass, its relaxed-condition corkscrew shape becomes entwined in the random vaso-occlusion winding. Withdrawing the catheter and retrieving wire from the site then acts to knot the two coiled wires together, allowing the vaso-occlusion wire to be withdrawn.

From the foregoing, it can be appreciated how various objects and features of the invention are met. The vaso-occlusion wire of the invention, both because of its relatively smooth surface and its flexible construction, can be advanced through sharp bends in a small-diameter catheter, allowing wire placement in small vessels positioned in a tortuous vessel path. The irregular winding conformation of the wire insures the formation of a randomly coiled space-filling mass in the vessel, when the wire is released from the catheter. The wire can be designed for depot delivery of drugs, e.g., to combine vaso-occlusion and drug therapy at a tumor region.

The vaso-occlusion system of the invention allows for placement of a permanent, space-filling vaso-occlusion mass in small-diameter, difficult-to-reach vessels. The method of the invention also provides for backfilling with a drug-containing bolus, to achieve temporary drug release from the site, combined with permanent vaso-occlusion. Finally, the method can be practiced to retrieve a vaso-occlusion wire from a vessel, once the purpose of the occlusion has been served.

Although the invention has been described with respect to specific embodiments and uses, it will be appreciated that various modifications in construction and use can be made without departing from the invention. For example, it is contemplated that the vaso-occlusion wire can be used for contraceptive purposes as an intrauterine device (IUD), by wire placement within the Fallopian tube of a woman.

It is claimed:

1. A flexible, vaso-occlusive wire designed for occluding a vessel having a selected cross-sectional area, when the wire is released into the vessel from a small-diameter catheter, said wire being characterized by:
    (a) a relaxed condition in which the wire assumes a folded, convoluted conformation which is adapted to form a substantially space-filling body having a substantially predetermined diameter when the wire is in said released condition,
    (b) a stretched condition in which the wire has a linear conformation in which the wire can be pushed through said catheter, and
    (c) a memory which returns the wire from its stretched to its relaxed condition, as the wire is released from said catheter in the vessel, thereby forming a space-filling, vaso-occlusive body which is lodged in the vessel at the site of release, the size of the wire and relaxed shape of the body being such as to occlude the vessel at said site.

2. The wire of claim 1, which, in its stretched condition, is an elongate helically coiled wire formed by wrappings of a metal thread, and the coiled wire, in its stretched condition, has a length which is at least about 15-20 times the diameter of the space-filling body formed when the wire is in said relaxed condition.

3. The wire of claim 2, wherein the diameter of the coil is between about 10-30 mils and the metal thread is platinum, tungsten, or gold.

4. The wire of claim 1, which is formed of a shape-memory polymer.

5. The wire of claim 4, which is formed of a tubular polymer, and the tube contains a drug intended for slow release.

6. The wire of claim 4, wherein the polymer is coated with a drug that is released slowly from the polymer within a vessel site.

7. The wire of claim 2, whose relaxed conformation is characterized by a helical windings of the coiled wire, and a tertiary structure formed by irregular bends in the winding.

8. The wire of claim 7, wherein the diameter of the helical winding is substantially the same as that of the vessel to be occluded.

9. The wire of claim 7, wherein the irregularities in the helical winding take the form of angular offsets in the helical axis.

10. The wire of claim 7, wherein the helical winding has a spiral shape dimensioned to fill the cross sectional area of the vessel to be occluded.

11. The wire of claim 7, wherein the diameter of the coil is between about 10-30 mils, the diameter of the secondary coiled conformation is substantially the same as that of the vessel to be occluded and the metal thread forming the wire is platinum, gold, or tungsten.

12. The wire of claim 11, for occlusion of a 0.5-2 mm diameter vessel, wherein the length of the wire, in its stretched condition, is about 3-6 cm.

13. The wire of claim 11, for occlusion of a vessel about 3-6 mm in diameter, wherein the length of the wire, in its stretched condition, is about 4-9 cm.

14. A flexible, vaso-occlusive wire designed for occluding a vessel having a selected cross-sectional area, when the wire is released into the vessel from a small-diameter catheter, said wire being characterized by:
   (a) a stretched, substantially linear condition in which the wire can be pushed through the catheter;
   (b) a relaxed, substantially convoluted condition formed by a combination of a helical winding in the wire which has a winding diameter substantially that of the vessel to be occluded, and irregularities in the helical winding which cause the wire to assume a substantially random, space filling body when released from a catheter into the vessel,
   (c) a memory which returns the wire from its stretched to its relaxed condition, as the wire is released from said catheter in the vessel, thereby to form a space-filling, vaso-occlusive body which is lodged in the vessel at the site of release, the size of the wire and relaxed shape of the body being such as to occlude the vessel at said site.

15. The wire of claim 14, which is an elongate helically coiled wire formed by wrappings of a metal thread, and the coiled wire, in its stretched condition, has a length which is at least about 15-20 times the diameter of the space-filling body formed when the wire is released into said vessel.

16. The wire of claim 15, wherein the diameter of the coiled wire is between about 10-30 mils, and the metal thread forming the wire is platinum, gold, or tungsten.

17. A catheter system for use in occluding a vessel having a selected cross-sectional area, said system comprising:
   (i) a catheter having a small-diameter inner lumen and designed to access a selected site of occlusion in said vessel,
   (ii) a flexible vaso-occlusive wire characterized by:
      (a) a stretched, substantially linear condition in which the wire can be pushed through said catheter;
      (b) a relaxed, substantially convoluted condition formed by a combination of a helical winding in the wire which has a winding diameter substantially that of the vessel to be occluded, and irregularities in such helical winding which cause the wire to assume a substantially random, space filling body when released from the catheter into the vessel,
      (c) a memory which returns the wire from its stretched to its relaxed condition, as the wire is released from such catheter in the vessel, thereby to form a space-filling, vaso-occlusive mass which is lodged in the vessel at the site of release, and
   (d) a pusher for advancing the wire in its stretched condition through the catheter to the selected site of occlusion.

18. The system of claim 17, wherein the wire is an elongate helically coiled wire formed by wrappings of platinum, gold, or tungsten thread, and the coiled wire, in its stretched condition, has a length which is at least about $15 \geqq 20$ times the diameter of the space-filling mass formed when the wire is released into the vessel.

19. The system of claim 17, wherein the pusher has a relatively long, relatively stiff metal wire proximal region, and a relatively short relatively flexible distal region formed of a low-friction polymer tubing.

20. The system of claim 19, wherein the polymer tubing is an extruded fluorocarbon polymer tubing.

21. The system of claim 19, wherein the combined diameter of the distal region of the pusher and the vaso-occlusive wire is greater than the inner lumen diameter of the catheter.

22. A method of occluding a selected site in a vessel having an inner lumen diameter of between about 2-4 mm, said method comprising
   accessing the site with a catheter having a small-diameter lumen,
   advancing through the catheter, a flexible vaso-occlusive wire characterized by:
      (a) a stretched, substantially linear condition in which the wire can be pushed through said catheter;
      (b) a relaxed, substantially convoluted condition formed by a combination of a helical winding in the wire which has a winding diameter substantially that of the vessel to be occluded, and irregularities in such helical winding which cause the wire to assume a substantially random, space filling body when released from a catheter into the vessel,
      (c) a memory which returns the wire from its stretched to its relaxed condition, as the wire is released from said catheter in the vessel, and
   releasing the wire from the catheter at the vessel, thereby forming a space-filling, vaso-occlusive body which is lodged in the vessel at the site of release.

23. The method of claim 22, wherein the wire is an elongate helically coiled wire formed by wrappings of a platinum, gold, or tungsten thread, and the coiled wire, in its stretched condition, has a length which is at least about 15-20 times the diameter of the space-fillig body formed when the wire is released into the vessel.

24. The method of claim 22, for use in slow-release drug delivery at the vaso-occlusion site, wherein the wire contains a drug adapted for slow release into the vessel site.

25. The method of claim 22, for use in slow-release drug delivery at the vaso-occlusion site, which further includes injection a bolus of drug-containing vaso-occlusion material immediately upstream of the vaso-occlusion wire in the vessel.

* * * * *